US009351807B2

(12) United States Patent
Höscheler

(10) Patent No.: US 9,351,807 B2
(45) Date of Patent: May 31, 2016

(54) LITHIUM SILICATE GLASS CERAMIC MATERIAL, PROCESS OF PRODUCTION AND USE THEREOF

(71) Applicant: 3M INNOVATIVE PROPERTIES COMPANY, Saint Paul, MN (US)

(72) Inventor: Stefan Höscheler, Munich (DE)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 0 days.

(21) Appl. No.: 14/356,761

(22) PCT Filed: Dec. 6, 2012

(86) PCT No.: PCT/US2012/068238
§ 371 (c)(1),
(2) Date: May 7, 2014

(87) PCT Pub. No.: WO2013/086187
PCT Pub. Date: Jun. 13, 2013

(65) Prior Publication Data
US 2014/0322503 A1      Oct. 30, 2014

(30) Foreign Application Priority Data
Dec. 8, 2011   (EP) ..................................... 11192534

(51) Int. Cl.
*B28B 7/02* (2006.01)
*C03C 1/00* (2006.01)
(Continued)

(52) U.S. Cl.
CPC ... *A61C 5/08* (2013.01); *A61C 5/10* (2013.01); *A61C 7/12* (2013.01); *A61C 8/0012* (2013.01); *A61C 13/0006* (2013.01); *A61C 13/081* (2013.01); *A61K 6/023* (2013.01); *A61K 6/024* (2013.01); *A61K 6/025* (2013.01); *A61K 6/0215* (2013.01); *A61K 6/0235* (2013.01); *A61K 6/0245* (2013.01); *A61K 6/0255* (2013.01);
(Continued)

(58) Field of Classification Search
None
See application file for complete search history.

(56) References Cited

U.S. PATENT DOCUMENTS

| 4,515,634 | A | 5/1985 | Wu |
| 5,219,799 | A | 6/1993 | Beall |

(Continued)

FOREIGN PATENT DOCUMENTS

| CA | 2213390 | 5/1998 |
| DE | 2451121 | 7/1975 |

(Continued)

OTHER PUBLICATIONS

International Search Report for PCT International Application No. PCT/US2012/068238 mailed on Jan. 28, 2013, 4 pages.

(Continued)

*Primary Examiner* — David Sample
*Assistant Examiner* — Nicole T Gugliotta
(74) *Attorney, Agent, or Firm* — 3M Innovative Properties Company; Eric E. Silverman

(57) ABSTRACT

The invention relates to a lithium silicate glass ceramic comprising $CsO_2$ in an amount from about 6 to about 30 wt.-%. The invention also relates to a three-dimensional article comprising at least two layers (I) and (II), each layer (I) and (II) comprising a lithium silicate glass ceramic, the lithium silicate glass ceramics of layer (I) having a different translucency than the lithium silicate glass ceramic of layer (II).

17 Claims, 1 Drawing Sheet

(51) Int. Cl.

| | |
|---|---|
| *C03C 10/12* | (2006.01) |
| *A61C 5/08* | (2006.01) |
| *A61K 6/027* | (2006.01) |
| *C03C 4/00* | (2006.01) |
| *C03C 10/00* | (2006.01) |
| *A61K 6/02* | (2006.01) |
| *A61C 5/10* | (2006.01) |
| *A61C 7/12* | (2006.01) |
| *A61C 8/00* | (2006.01) |
| *A61C 13/00* | (2006.01) |
| *A61C 13/08* | (2006.01) |
| *C03C 3/095* | (2006.01) |
| *C03C 3/097* | (2006.01) |

(52) U.S. Cl.
CPC .............. *A61K 6/0273* (2013.01); *C03C 3/095* (2013.01); *C03C 3/097* (2013.01); *C03C 4/0021* (2013.01); *C03C 10/00* (2013.01); *C03C 10/0027* (2013.01); *C03C 2204/04* (2013.01); *C03C 2205/02* (2013.01); *C03C 2205/06* (2013.01); *Y10T 428/24942* (2015.01)

(56) References Cited

U.S. PATENT DOCUMENTS

| | | | |
|---|---|---|---|
| 6,133,174 A | 10/2000 | Brodkin | |
| 6,155,830 A | 12/2000 | Brodkin | |
| 6,420,288 B2 | 7/2002 | Schweiger | |
| 6,484,791 B1 | 11/2002 | Vidal | |
| 6,517,623 B1 | 2/2003 | Brodkin | |
| 6,709,694 B1 | 3/2004 | Suttor | |
| 6,713,421 B1 | 3/2004 | Hauptmann | |
| 6,769,912 B2 | 8/2004 | Beuschel | |
| 6,802,894 B2 | 10/2004 | Brodkin | |
| 7,118,085 B2 | 10/2006 | Foser | |
| 8,536,078 B2 | 9/2013 | Ritzberger | |
| 8,778,075 B2 | 7/2014 | Ritzberger | |
| 2003/0132539 A1 | 7/2003 | Althoff | |
| 2004/0119180 A1 | 6/2004 | Frank | |
| 2005/0054509 A1 | 3/2005 | Hoen | |
| 2009/0004271 A1 | 1/2009 | Brown | |
| 2009/0256274 A1 | 10/2009 | Castillo | |
| 2010/0083706 A1 | 4/2010 | Castillo | |
| 2011/0256409 A1 * | 10/2011 | Ritzberger et al. | 428/432 |
| 2012/0241991 A1 | 9/2012 | Ritzberger | |

FOREIGN PATENT DOCUMENTS

| | | | |
|---|---|---|---|
| EP | 0455854 | 11/1991 | |
| EP | 0536479 | 4/1993 | |
| EP | 2500009 | 9/2012 | |
| GB | 924996 | 5/1963 | |
| WO | WO 99-18910 | 4/1999 | |
| WO | WO 99-45889 | 9/1999 | |
| WO | WO 2011/041194 A1 * | 4/2011 | A61C 13/00 |
| WO | WO 2011/146761 * | 11/2011 | A61K 6/027 |

OTHER PUBLICATIONS

Appen, A A, Berechnung der optischen Eigenschaften, der Dichte und des Ausdehnungskoeffizenten von Silikatgläsern aus ihren Zusammensetzungen, Ber. Akad. Wiss. UDSSR 69 (1949) 841-844.
H.Scholze Glas—Natur, Struktur und Eigenschaften, zweite Aufgale pp. 144-149 Berlin, Heidelberg 1977.
H.Scholze Glas—Natur, Struktur und Eigenschaften, zweite Aufgale pp. 177-180 Berlin, Heidelberg 1977.
Lithium Disilicate, Lithium, 241 (1927).

* cited by examiner

LITHIUM SILICATE GLASS CERAMIC MATERIAL, PROCESS OF PRODUCTION AND USE THEREOF

CROSS REFERENCE TO RELATED APPLICATIONS

This application is a national stage filing under 35U.S.C. 371of PCT/US2012/068238, filed Dec. 6, 2012, which claims priority to European Application No. 11192534.3, filed Dec. 8, 2011, the disclosures of which are incorporated by reference in their entirety herein.

FIELD OF THE INVENTION

The invention relates to lithium silicate glass ceramic materials and their use in the dental field, especially for producing dental restorations. The invention also relates to dental milling blocks and ingots comprising a lithium silicate glass ceramic material.

BACKGROUND ART

Lithium silicate materials are known for a long time and used for various applications, in particular in the dental area for producing dental restorations.

US 2010/0093706 (Castillo) and US 2009/0256274 (Castillo) relate to lithium silicate glass ceramic materials for the manufacture of blocks for dental appliances using a CAD/CAM process. The lithium silicate materials include from 1 to 10 wt.-% germanium dioxide. The materials are said to have improved castability and higher density.

US 2009/0042717 (Apel et al.) describes lithium silicate materials which are said to be easily millable and having a high strength. The lithium silicate materials contain Me(II)O being selected from CaO, BaO and SrO and less than 0.1 wt.-% ZnO.

U.S. Pat. No. 6,420,288 B2 (Schweiger et al.) deals with a process for the preparation of shaped translucent lithium disilicate glass ceramic products, which comprises producing a melt of a starting glass containing $SiO_2$ (57.0 to 80.0 wt.-%), $Al_2O_3$ (0 to 5.0 wt.-%), $La_2O_3$ (0.1 to 6.0 wt.-%), MgO (0 to 5.0 wt.-%), ZnO (0 to 8.0 wt.-%) and $Li_2O$ (11.0 to 19.0 wt.-%). It is mentioned that the additional incorporation of $ZrO_2$ let to an increase in translucency.

US 2005/0054509 (Hoen et al.) relates to a translucent and radio-opaque glass ceramic which may comprise $Li_2O$ from 0 to 3 wt.-%, $Na_2O$ from 0 to 9.0 wt.-%, $K_2O$ from 3.0 to 14.0 wt.-%, $Rb_2O$ from 0 to 12.5 wt.-% and $Cs_2O$ from 0 to 18.0 wt.-%. It is stated that the main crystalline phase is apatite, in particular a Ca-apatite where Ca is totally or partially replaced by Sr and/or Mg.

U.S. Pat. No. 6,155,830 (Brodkin et al.) describes a dental restoration comprising a porcelain composition comprising a glassy matrix and leucite crystallites embedded therein. The coefficient of thermal expansion (CTE) is said to be in a range from 12 to $15*10^{-6}/°$ C. The content of $Li_2O$ is in a range of 0 to 3 wt.-%.

EP 2 377 830 A1 describes a lithium silicate glass ceramic comprising at least 8.5 wt.-% transition metal oxides selected from oxides of yttrium and oxides of the transition metals having the numbers 41 to 79.

U.S. Pat. No. 6,133,174 (Brodkin et al.) deals with a method of producing a machinable feldspathic porcelain composition comprising leucite. The content of $Li_2O$ of the composition is said to be within a range from 0 to 3 wt.-%. The 3-point bending strength measured is within a range from 127 to 136 MPa.

WO 99/18910 (Jeneric Pentron) relates to a dental porcelain composition comprising a continuous glassy phase and a discontinuous, substantially crystalline phase comprising cubic leucit. The porcelain exhibits a coefficient of thermal expansion in the range of 11 to $17*10^{-6}/°$ C. The $Li_2O$ content of the raw material is said to be from 1.5 to 4 mol.-%.

However, there is still a need for lithium silicate glass ceramic materials which facilitate the production of multi-layered milling blocks comprising a translucent layer of material.

DESCRIPTION OF INVENTION

Figure 1:
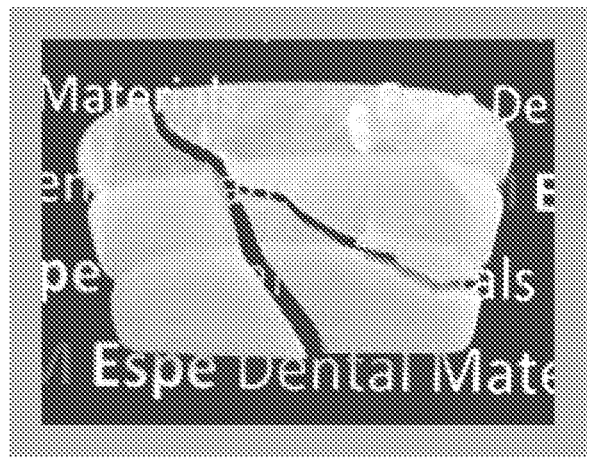
FIG. 1 is a cracked multi-layered block.

Thus, it is an object of the invention to facilitate the production of multi-layered blocks, especially blocks containing at least one layer comprising a lithium silicate glass ceramic with a high translucency.

Besides this object or in addition thereto, a further object can be seen in providing a variety of lithium silicate glass ceramic material(s) having similar coefficients of thermal extension (CTE) but differing in their translucency.

It was found that at least one of the objects outlined above can be achieved by providing a lithium silicate glass ceramic, especially a lithium disilicate glass ceramic containing $Cs_2O$ in an amount from about 6 to about 30 wt.-% or from about 7 to about 25 wt-.% or from about 8 to about 20 wt.-% or from about 8 to about 15 wt.-%, wt.-% with respect to the weight of the whole glass ceramic.

The invention also relates to a lithium silicate glass ceramic comprising the following components
$SiO_2$ from about 55 to about 80 wt.-%,
$Al_2O_3$ from about 1 to about 5 wt.-%,
$Li_2O$ from about 7 to about 16 wt.-%,
$Cs_2O$ from about 6 to about 30 wt.-%,
$P_2O_5$ from about 1 to about 5 wt.-%,
wt.-% with respect to the weight of the glass ceramic.

Upon application of a transformation step (e,g, application of a heating step and/or an annealing step), the lithium silicate glass ceramic can be transferred or transformed into a lithium disilicate glass ceramic.

A further aspect of the invention is directed to a method of producing a lithium silicate glass ceramic as described the present text, the method comprising the steps of:
melting the composition,
fining the composition e.g. at about 1500 to about 1600° C. for about 5 to 30 min,
annealing the composition e.g. at about 500 to about 600° C. for about 30 min to about 2 h,
heating the composition e.g. to about 600 to about 700° C. for about 1 to about 30 h (nucleation step),
optionally cooling the composition down to room temperature,
heating the composition e.g. to about 800 to about 900° C. for about 10 min to about 2 h (crystallization step),
cooling the composition down to room temperature.

The invention also relates to a three-dimensional article having the shape of a dental mill blank or ingot comprising a lithium silicate glass ceramic as described in the present text.

The invention also relates to the use of the lithium silicate ceramic or the dental mill blank as described in the present text for producing dental restorations.

According to another aspect, the invention relates to kit of parts comprising a part A and a part B, part A comprising a lithium silicate ceramic or the dental mill blank as described in the present text and part B comprising a zirconia based ceramic article.

The invention also relates to a dental restoration comprising at least two sections A and B, section A comprising a zirconia based ceramic and section B comprising a lithium silicate based ceramic as described in the present text.

It was found that by adding Cs2O to the glass matrix the CTE value can easily be adjusted. This facilitates the production of materials and compositions having a similar expansion behavior if heated. On the other hand the refractive index (n) of the material hand is typically not negatively affected.

Using the inventive materials also enables the skilled person to produce multi-layered blocks, especially multi-layered blocks containing at least one layer having a high translucency.

Due to the finding that compositions containing a certain amount of Cs2O have similar CTE values, the layers of the multi-layered blocks adhere together well during heating without cracking.

Thus, using Cs2O containing lithium silicate materials facilitates the production of multi-layered blocks having less internal stress and/or tensions.

Further, in contrast to other lithium silicate materials, the present material is sufficiently x-ray opaque, thus the material is visible when applying x-ray methods.

It was also found that the addition of Cs2O often results in a lower viscosity of the composition at a given temperature. This may facilitate the production of dental milling blocks and ingots. A lower viscous composition has a better flowability and allows also the production of more complicated shaped blocks (e.g. blocks in segment form; blocks having angles less than 90°; etc.).

Unless defined differently, for this description the following terms shall have the given meaning:

The term "dental article" means any article which can and is to be used in the dental field, especially dental restorations and parts thereof. Dental restorations often comprise at least two parts: a dental support structure (sometimes also referred to as frame or coping) and a dental facing. Examples of dental articles include crown(s), bridge(s), veneer(s), facing(s), implant(s), abutment(s), root-pin(s), orthodontic bracket(s), dental support structure(s), inlay(s), onlay(s), full arch prosthese(s), monolithic structures and parts thereof.

The material the dental article is made of should not be detrimental to the patient's health and thus free of hazardous and toxic components being able to migrate out of the article. Dental articles are typically of small size and may comprise sections having a wall thickness in the range of about 100 μm to 2,000 μm or in the range of about 100 mm to about 500 μm. The total volume of a dental article is typically below about 100 ml or below about 50 ml or below about 10 ml or below about 5 ml.

A "support structure" is to be understood as a structure being suitable to support or stabilize another article.

A "dental support structure" is to be understood as the part of a dental restoration which is typically adhered to a tooth stump or inserted into the patients mouth and suitable for being veneered by a dental facing or dental veneer. A dental support structure has typically sufficient strength to withstand chewing forces.

Dental support structures are often made of or comprise oxide ceramic materials including $ZrO_2$, and $Al_2O_3$, metals or alloys. Compared to other framework such as pottery or paving stones, the dental framework is small and filigree and of high strength. The thickness of the dental framework can vary from very thin, e.g. at the edges and rims (below about 0.1 mm) to considerably thick, e.g. in the biting area (up to about 7 mm). However, dental frameworks may also be made of or comprise metal or metal alloys.

The term "dental facing" or "dental veneer" refers to the aesthetic part of a dental restoration, meaning the part comprising an outer surface of the finished restoration. The dental facing is further adapted to be applied to a frame or dental support structure which forms another part of the dental restoration, and the dental restoration is in turn applied to a tooth. The dental facing is preferably arranged at those parts of the dental support structure that are likely to be visible in a patient's mouth, or that in particular functionally co-operate with the adjacent or opposed teeth of a patient, for example. Dental veneers are also small and filigree objects. The strength of dental veneers, however, is typically lower compared to dental frameworks. Dental veneers are typically made of or comprise glass or glass ceramic materials.

A dental support structure or a dental veneer usually has a 3-dimensional inner and outer surface including convex and concave structures. The outer surface of the dental framework typically corresponds essentially to the inner surface of the dental veneer. The inner surface of the dental framework typically corresponds essentially to the outer surface of a prepared tooth stump, whereas the outer surface of the dental veneer typically corresponds essentially to the final dental restoration.

By "dental mill blank" is meant a solid block (3-dim article) of material from which a dental article can be machined. A dental mill blank may have a size of about 20 mm to about 30 mm in two dimensions, for example may have a diameter in that range, and may be of a certain length in a third dimension. A blank for making a single crown may have a length of about 15 mm to about 30 mm, and a blank for making bridges may have a length of about 40 mm to about 80 mm. A typical size of a blank as it is used for making a single crown has a diameter of about 24 mm and a length of about 19 mm. Further, a typical size of a blank as it is used for making bridges has a diameter of about 24 mm and a length of about 58 mm. Besides the above mentioned dimensions, a dental mill blank may also have the shape of a cube, a cylinder or a cuboid. Larger mill blanks may be advantageous if more than one crown or bridge should be manufactured out of one blank. For these cases, the diameter or length of a cylindric or cuboid shaped mill blank may be in a range of about 100 to about 200 mm, with a thickness being in the range of about 10 to about 30 mm.

An "ingot" means a block of material which can be melted. Such a block is typically used I a so-called "hot pressing technique". The ingot, which is usually embedded in an investment material, is heated to a certain temperature and the material converted into a viscous state. The viscous material is applied/pressed on the outer surface of a support structure.

A "powder" means a dry, bulk solid composed of a large number of very fine particles that may flow freely when shaken or tilted.

A "particle" means a substance being a solid having a shape which can be geometrically determined. The shape can be regular or irregular. Particles can typically be analysed with respect to e.g. grain size and grain size distribution.

"Glass" means an inorganic non-metallic amorphous material. Glass refers to a hard, brittle, transparent solid.

Typical examples include soda-lime glass and borosilicate glass. A glass is an inorganic product of fusion which has been cooled to a rigid condition without crystallizing. Most glasses contain silica as their main component and a certain amount of glass former. Glasses usually show an amorphous or diffuse X-ray pattern or diffraction.

"Glass-ceramic" means an inorganic non-metallic material where one or more crystalline phases are surrounded by a glassy phase so that the material comprises a glass material and a ceramic material in a combination or mixture. Thus, a glass ceramic is a material sharing many properties with both glass and crystalline ceramics. Usually, it is formed as a glass, and then made to crystallize partly by heat treatment. So, glass ceramics are made of a glassy phase with crystals, which typically have no pores in the glassy phase or between crystals. Glass ceramics mainly refer to a mixture of lithium-, silicon-, and aluminium-oxides.

"Ceramic" means an inorganic non-metallic material that is produced by application of heat. Ceramics are usually hard and brittle and, in contrast to glasses or glass ceramics, display an essentially purely crystalline structure.

A "ceramic article" is to be understood as an article comprising a ceramic, glass or glass ceramic material.

A "lithium silicate glass ceramic" means a material comprising quartz, lithium dioxide, phosphor oxide and alumina. A lithium silicate glass ceramic may comprise lithium metasilicate crystals ($Li_2SiO_3$), lithium disilicate crystals ($Li_2Si_2O_5$) or a mixture of both crystals. Lithium silicate glass ceramic comprising mainly lithium metasilicate crystals have typically a low strength and toughness compared to lithium silicate glass ceramic comprising mainly lithium disilicate crystals. Lithium silicate glass ceramic comprising mainly lithium metasilicate crystals can typically be machined easily. After a machining step, the material can be converted into a lithium disilicate glass ceramic material by a heating step.

A "lithium disilicate glass ceramic" means a material comprising mainly lithium disilicate crystals (e.g. content of crystalline lithium disilicate phase above about 50 or above about 55 or above about 60 or above about 65 vol.-%; typical ranges include from about 50 to about 90 or from about 55 to about 85 or from about 60 to about 80 vol.-%).

By "machining" is meant milling, grinding, cutting, carving, or shaping a material by a machine. Milling is usually faster and more cost effective than grinding.

A composition is "essentially or substantially free of" a certain component within the meaning of the invention, if the composition does not contain said component as an essential feature. Thus, said component is not wilfully added to the composition either as such or in combination with other components or ingredient of other components. A composition being essentially free of a certain component usually contains the component in an amount of less than about 1 wt.-% or less than about 0.1 wt.-% or less than about 0.01 wt.-% with respect to the whole composition. Ideally the composition does not contain the said component at all. However, sometimes the presence of a small amount of the said component is not avoidable e.g. due to impurities.

As used herein, "a", "an", "the", "at least one" and "one or more" are used interchangeably. The terms "comprises" or "contains" and variations thereof do not have a limiting meaning where these terms appear in the description and claims. Also herein, the recitations of numerical ranges by endpoints include all numbers subsumed within that range (e.g., 1 to 5 includes 1, 1.5, 2, 2.75, 3, 3.80, 4, 5, etc.).

Unless otherwise indicated, all numbers expressing quantities of ingredients, measurement of properties such as contrast ratio and so forth used in the specification and claims are to be understood as being modified in all instances by the term "about."

The inventive lithium silicate glass ceramic or the lithium disilicate glass ceramic contains $Cs_2O$ in an amount from about 6 to about 30 wt.-% or from about 7 to about 25 wt-.% or from about 8 to about 20 wt.-% or from about 8 to about 15 wt.-%, wt.-% with respect to the weight of the whole glass ceramic.

According to another embodiment, the lithium silicate glass ceramic may have the following composition:
$SiO_2$ from about 55 to about 80 wt.-%,
$Al_2O_3$ from about 1 to about 5 wt.-%,
$B_2O_3$ from 0 to about 2 wt.-%
$Li_2O$ from about 7 to about 16 wt.-%,
$Cs_2O$ from about 6 to about 30 wt.-%,
$P_2O_5$ from about 1 to about 5 wt.-%,
$SiO_2$ from about 55 to about 80 wt.-% or from about 60 to about 65 wt.-%,
$Al_2O_3$ from about 1 to about 5 wt.-% or from about 1 to about 2 wt.-%,
$B_2O_3$ from 0 to about 5 wt.-% or from about 0 to about 2 wt.-%,
$Li_2O$ from about 7 to about 16 wt.-% or from about 8 to about 13 wt.-%,
$Na_2O$ from 0 to about 1 wt.-% or from about 0.05 to about 0.2 wt.-%,
$Cs_2O$ from about 6 to about 30 wt.-% or from about 10 to about 15 wt.-%,
$P_2O_5$ from about 1 to about 5 wt.-% or from about 1.5 to about 3.0 wt.-%.

The lithium silicate glass ceramic described in the present text may also comprise from about 0.1 to about 10 wt.-% or from about 0.1 to about 8 or from about 0.1 to about 5 wt.-% of further metal oxides being selected from SrO, BaO, $TiO_2$, $ZrO_2$, $HfO_2$, $Fe_2O_3$, $VO_2$, $Y_2O_3$, $CeO_2$, $Sm_2O_3$, $Er_2O_3$, $Dy_2O_3$, or mixtures thereof.

The total amount of the metal oxide mentioned above which may be present in the lithium silicate glass ceramic described in the present text is typically below about 10 or below about 8 or below about 5 wt.-% with respect to the weight of the lithium silicate glass ceramic material.

Increasing the amount of these oxides to a value above about 5 or above about 8 or above about 10 wt.-% may negatively influence the balance of the desired properties, especially providing a material having sufficient translucency and a coefficient of thermal extension within a range from about 8 to about $-11*10^{-6}/°$ C.

According to a further embodiment, the following components might be present either alone or in combination with others.
SrO from 0.0 to about 5 wt.-% or from about 0.1 to about 3.0 wt.-%;
BaO from 0.0 to about 7 wt.-% or from about 0.1 to about 3.0 wt.-%;
$TiO_2$ from 0.0 to about 2 wt.-% or from about 0.1 to about 3.0 wt.-%;
$ZrO_2$ from 0.0 to about 4.0 wt.-% or from about 0.01 to about 0.05 wt.-%;
$HfO_2$ from 0.0 to about 5.0 wt.-% or from about 2.0 to about 4.0 wt.-%;
$Fe_2O_3$ from 0.0 to about 0.5 wt.-% or from about 0.1 to about 0.3 wt.-%;
$VO_2$ from 0.0 to about 0.5 wt.-% or from about 0.01 to about 0.3 wt.-%;
$Y_2O_3$ from 0.0 to about 1.5 wt.-% or from about 0.1 to about 1.0 wt.-%;

CeO2 from 0.0 to about 3.0 wt.-% or from about 0.1 to about 2.0 wt.-%;
Sm2O3 from 0.0 to about 2.0 wt.-% or from about 0.0 to about 1.0 wt.-%;
Er2O3 from 0.0 to about 2.0 wt.-% or from about 0.01 to about 0.4 wt.-%;
Dy2O3 from 0 to about 1.0 wt.-% or from about 0.1 to about 0.2 wt.-%;
K2O from 0 to about 0.1 wt.-% or from about 0.001 to about 0.002 wt.-%;
MgO from 0 to about 0.2 wt.-% or from about 0,002 to about 0.01 wt.-%;
ZnO from 0 to about 0.2 wt.-% or from about 0,002 to about 0.01 wt.-%;
La2O3 from 0 to about 0.1 wt.-% or from about 0.0001 to about 0.01 wt.-%;
wt.-% with respect to the weight of the lithium silicate material.

Certain of these oxides may fulfill specific functions during the production process:
  SiO2 may function as a network former and lithium silicate precursor.
  Al2O3 may increase the chemical stability of the glass matrix.
  Li2O may act as lithium silicate precursor.
  Cs2O may function as fluxing agent and may help to control the phase separation and increase the radiopacity.
  P2O5 may function as nucleating agent.
  CeO2 may act as oxidative colouring stabilizer.
  Er2O3 may act as a colour adjusting agent (e.g. to reduce the greenish colour fault).
  BaO, SrO, Y2O3, ZrO2 and HfO2 can be used to adjust the refractive index of the glass matrix.

A composition comprising essentially the oxides of SiO2, Al2O3, Li2O, Cs2O, P2O5 can sometimes be preferred.

The oxides of SrO, BaO, TiO2, ZrO2, HfO2, Fe2O3, VO2, Y2O3, CeO2, Sm2O3, Er2O3, Dy2O3, or mixtures thereof have a comparable high influence on the overall refractive index and thus can be used to adjust the translucency of the composition, if desired.

Coloured oxides including Fe2O3, Mn2O3, VO2, CeO2, Sm2O3, Er2O3, Dy2O3, or mixtures thereof can (also) be used to adjust the colouring of the composition.

According to one embodiment, the lithium silicate glass ceramic comprises besides Cs2O also CeO2 (e.g. about 0.1 to about 2.0 wt.-%) and Er2O3 (e.g. about 0.01 to about 0.4 wt.-%).

The inventive lithium silicate glass ceramic does typically not comprise K2O, MgO, ZnO, La2O3 or a mixture of those in an amount above about 0.5 wt.-% or above about 0.4 wt.-% or above about 0.3 wt.-% or above about 0.2 wt.% or above about 0.1 wt.-% with respect to the weight of the ceramic.

According to a particular embodiment, the lithium silicate glass ceramic does not comprise K2O in an amount above about 0.4 wt.-% or above about 0.3 wt.-% or above about 0.2 wt.% or above about 0.1 wt.-% with respect to the weight of the ceramic.

The Li2O content is typically below about 15 wt.-% or below about 14 wt.-% with respect to the weight of the glass ceramic.

Reducing the amount of either of oxides K2O, MgO, ZnO, La2O3 may facilitate the production of a translucent ceramic material having the desired CTE value.

The lithium silicate glass ceramic material described in the present text has a composition which can be transferred into a lithium disilicate glass ceramic material. This is typically done by applying a heating step. Such a heating step may facilitate the further crystallisation of the composition.

The lithium silicate glass ceramic described in the present text does typically not comprise either of the following crystal phases in an amount above about 50 or above about 40 or above about 30 or above about 20 or above about 10 or above about 5% (at room ambient conditions; e.g. 23° C.): apatite, tetragonal or cubic leucit.

The inventive lithium silicate glass ceramic material (or at least one layer thereof, if the material is part of a multi-layered block) may fulfill at least one of the following parameters:
  translucency from about 0.03 to about 0.60 or from about 0.1 to about 0.4 (Mac Beth TD 932 sample thickness 1.50+/−0.05 mm polished with 9 μm sandpaper); a translucency of 0.0 means that the sample is fully transparent.
  radiopacity of more than about 200%, or more than about 300% (according to ISO 6872);
  coefficient of thermal expansion from about 8.0 to about $12*10^{-6}$/K or from about 8.0 to about $11*10^{-6}$/K or from about 9.0 to about $10.4*10^{-6}$/K (according to ISO 6872);
  Vickers hardness of at least about 500 or at least about 520 or at least about 550 (HV; 0.2 kg);
  flexural strength of at least about 250 MPa or at least about 350 or at least about 400 (according to ISO 6872);
  refractive index in the range of about 1.545 to about 1.525 or in the range of about 1.530 to about 1.540 (measured with an Abee Refractometer).

If desired, the respective parameters can be determined as outlined in the example section below.

A lithium silicate glass ceramic material fulfilling the parameters coefficient of thermal expansion (CTE) and translucency as outlined above can sometimes be preferred. Such a material may facilitate the production of a sufficiently stable multi-layered block comprising at least one transparent layer.

Generally, the inventive material can be obtained by a process wherein the material is melted and heat treated in one or more steps. The heat treatment(s) typically lasts for at least about 30 min at a temperature(s) between about 500 to about 900° C.

In can sometimes be preferred, if the heat treatment (nucleation/crystallization step) is done in two steps:
i) for about 1 h to about 20 h at a temperature between about 600 and about 700° C. or for about 4 to about 20 h at a temperature between about 620 and about 680° C.,
ii) ii) for about 10 to about 60 min at about 750 to about 900° C. or for about 10 min to about 40 min at a temperature of about 800 to about 880° C.

More particularly, the material can be prepared by a process comprising the following steps:
a) melting the composition, optionally casting the composition into a mould,
b) fining the composition,
c) cooling the composition down to room temperature, optionally removing from the mould (e.g. in order to prepare sample preparation),
d) annealing the composition,
e) heating the composition (nucleation step),
f) optionally cooling down the composition to room temperature (e.g. for further sample preparation, if desired),
g) heating the composition (crystallization step),
h) cooling the composition down to room temperature.

Educts or starting materials for the preparation of the glass ceramic material which can be used include the carbonates, oxides, sulfates and phosphates of the respective metals. In particular, the following components can be used as starting materials:

Al2O3 aluminium hydroxide
B2O3 boric acid
Li2O lithium carbonate and lithium orthophosphate
P2O5 lithium orthophosphate
SiO2 quartz
SrO strontium carbonate
BaO barium carbonate
Cs2O caesium carbonate
TiO2 titan(IV)oxid
ZrO2 zircon oxide
Hf2O hafnium oxide
Sm2O3 samarium oxide
Er2O3 erbium oxide
Y2O3 yttrium oxide
Dy2O3 dysprosium oxide
VO2 vanadium(IV)oxide
Fe2O3 iron(III)oxide Na2SO4 is often added as a fining agent (e.g. from about 0.2 to about 1 wt.-% or from about 0.3 to about 0.8 wt.-% with respect to the weight of the whole composition). Colouring oxides can be added as needed and desired.

The composition is typically obtained by first mixing and/or milling of the components of the composition. This can be done under dry or wet conditions, e.g. using a ball mill.

If the mixing and/or milling is done under wet conditions a solvent is typically added. Solvents which can be used include water and alcohols like iso-propanol and ethanol. Mixing is typically done in a plastic (e.g. PE, PP) container.

The milling step is typically performed for about 30 to about 90 min.

The melting step(s) is(are) typically performed for about 0.5 to about 3 h or from about 1 h to about 2 h.

The melting temperature is typically from about 1400 to about 1600° C. or from about 1500 to about 1600° C.

In order to obtain a homogeneous composition, the melting step can be repeated, if desired.

Thus, there can be a $1^{st}$ melting step (e.g. about 5 to about 20 min; about 1500° C.), followed by a $1^{st}$ crushing step (where the molten composition is poured into water), followed by a $2^{nd}$ melting step (e.g. 20 min to 40 min; about 1500° C.), followed by a $2^{nd}$ crushing step, followed by a $3^{rd}$ melting step (e.g. 20 min to 40 min; about 1500° C.).

The molten composition is typically casted into a mould. The shape and volume of the mould is not particularly limited and typically depends on the amount of glass ceramic which should be produced. Moulds are often made of materials comprising or consisting of boron nitride, graphite, steel or combinations thereof.

The fining step is typically done for about 5 to 30 min at a temperature from about 1500 to about 1600° C. During the fining step, typically gaseous components are removed.

The annealing step is typically done for about 0.5 to about 12 h or from about 1 to about 2 h at a temperature within a range from about 450 to about 600° C.

The annealing step typically also comprises the step of cooling the composition to room temperature. This cooling step typically lasts for about 5 to about 12 h. During the cooling step, the material is typically left within the furnace.

The further heating step is typically used to initiate or facilitate the crystallization process. During this process usually meta silicate crystals are formed (nucleation step).

This nucleation step can be done for about 1 to about 35 h or from about 5 to about 20 h at a temperature within a range from about 500 to about 700° C. or from 550 to about 700° C. or from 600 to 700° C.

If desired, thereafter the composition may be cooled down to room temperature again. This may take from about 5 to about 20 h or from about 8 to about 15 h. This cooling step, however, is optional.

A further heating step is conducted (crystallization step) to initiate or facilitate the creating of disilicate crystals. The crystallization step is typically done at a higher temperature than the nucleation step.

This heating step can be done for about 10 min to about 60 min or from about 20 to about 40 min at a temperature within a range from about 700 to about 950° C. or from about 750 to about 900° C. or from about 800 to about 900° C.

Thereafter, the composition is again cooled down to room temperature. This may take from about 5 to about 20 h or from about 8 to about 15 h.

If desired, the phase transformation and formation of crystallites can be analyzed with differential scanning calorimetry and/or X-ray diffraction analysis.

The production of multi-layered blocks can be done in a similar manner. Multi-layered dental mill blanks or blocks can be produced by casting individual layers of molten lithium silicate material into a mould.

It can be advantageous, if the first layer of material is first cooled down to a certain temperature (e.g. about 700 to about 800° C.) before the second layer of material is applied. This may help reducing the risk of cracks.

In order to facilitate the production of highly esthetic dental articles, it can be useful, if at least one of the layers of the multi-layered dental mill blank has a high translucency.

More particularly, two or more crucibles containing the respective compositions are heated to the desired temperature. The $1^{st}$ composition (molten) is casted into a mould, thus obtaining a $1^{st}$ layer of material. The $1^{st}$ composition is cooled to about 700 to about 800° C. Thereafter, a $2^{nd}$ composition (molten) is casted on top of the $1^{st}$ layer of material. The $2^{nd}$ composition is cooled to about 700 to about 800° C.; and so on.

These steps can be repeated, if desired, in order to obtain a multi-layered block (e.g. containing at least 2, 3, 4, 5, 6 or even more layers):

Thereafter, the multi-layered composition is typically subjected to an annealing step, a nucleation step and a crystallization step.

The lithium silicate glass ceramic and especially the lithium disilicate glass ceramic described in the present text can be used for producing dental articles.

Dental articles which can be produced include crown(s), bridge(s), veneer(s), facing(s), implant(s), abutment(s), root-pin(s), orthodontic bracket(s), dental support structure(s), inlay(s), onlay(s), full arch prosthese and parts or combinations thereof.

Especially the combination of the lithium silicate glass ceramic with zirconia based structures can be beneficial. The zirconia based structure may function as a support structure on which a lithium silicate glass ceramic is applied, e.g. in the shape of a veneer, inlay, onlay, facing, facet or abutment.

The dental restorations or parts thereof can be produced from a dental mill blank or using a dental mill blank.

The dental mill blank can have different sizes and shapes.

The size of the dental mill blank is not particularly limited. Typical sizes for dental mill blanks include from about 10 mm to about 20 mm (width), from about 10 mm to about 25 mm (length) and from about 10 mm to about 20 mm (height).

The shape of the dental mill blank is not particularly limited, either. Typical shapes include blocks and pucks or cylinders (e.g. having a diameter or length/width from about 50 to about 150 mm and a height from about 10 mm to about 20 mm). If desired, also segments of pucks or cylinders can be made.

The dental mill blank is typically fixed in or to a holder, e.g. a frame or a stub. Fixing the mill blank to a holder may facilitate machining. The holder can be fixed to the mill blank in different ways including gluing or clamping. Examples thereof are described in US 2003/0132539, U.S. Pat. No. 6,769,912 and EP 0 455 854 B1, the content of which is herewith incorporated by reference.

Machining can be done using CAD/CAM technologies. Commercially available machines include those provided by the companies 3M ESPE, Sirona and others.

The dental mill blank can comprise only one layer or at least 2 layers or at least 3 layers or at least 4 layers of lithium silicate ceramics. The lithium silicate ceramics used for producing multi-layered blocks may differ in their translucency. The translucency of the lithium silicate ceramic can be adjusted e.g. by adding or varying the amount of Cs2O and also oxides having a high influence on the refractive index.

Thus, the invention also relates to a dental mill blank comprising at least two layers (I) and (II), each layer (I) and (II) comprising a lithium silicate glass ceramic as described in the present text, the lithium silicate glass ceramics of layer (I) having a different translucency than the lithium silicate glass ceramic of layer (II).

In order to facilitate the production of multi-layered dental mill blanks having less cracks, adjusting the CTE values of the materials of the individual layers can be beneficial.

The invention also relates to a dental mill blank comprising at least two layers (I) and (II), layer (I) comprising a lithium silicate glass ceramic (GC I) and layer (II) comprising a lithium silicate glass ceramic (GC II), the lithium silicate glass ceramics (GC I) and (GC II) being selected from lithium silicate glass ceramics as described the present text, the lithium silicate glass ceramics (GC I) and (GC II) having coefficients of thermal expansion (CTE I) and (CTE II) fulfilling the equation: $(CTE\ I)-(CTE\ II) \leq \pm 1.2*10^{-6}/K$.

It was found that a dental mill blank fulfilling this equation does typically show no or less cracks during the production process. Such a dental mill blank may also be sufficiently stable in order to be machined. The risk of chipping can be reduced. If the CTE values do not fulfill this equation, the likelihood of chipping is usually increased.

Alternatively, dental restorations can be produced by the so-called "hot pressing technique", which is known to the skilled person in the art. Such a technique is described e.g. in U.S. Pat. No. 6,484,791 (Vidal) or U.S. Pat. No. 7,118,085 (Foser et al.). The content of these documents as far as the hot pressing technique is concerned is herewith incorporated by reference.

Typically the ingot is subjected to a heat treatment until a viscous stage is reached. Useful temperatures include from about 700 to about 1200° C. During such a heat treatment, the ingot is typically embedded in an investment material.

The invention also relates to a kit of parts comprising a part A and a part B, part A comprising a lithium silicate ceramic or the dental mill blank as described the present text and part B comprising a zirconia based ceramic.

Zirconia based ceramics which can be used include materials comprising or consisting essentially of ZrO2. Further oxides like Al2O3 and/or HfO2 may be present as well. Useful zirconia based ceramics are typically stabilized with further oxides like Y2O3 or MgO.

Useful compositions are described in U.S. Pat. No. 6,709,694, US 2004/01191180, U.S. Pat. No. 6,713,421 and EP11158584.0. The content of these references with respect to the description of zirconia based ceramics is herewith incorporated by reference.

Like the present lithium silicate ceramics, the zirconia based ceramics can have the shape of a dental mill blank, too.

It was found that a dental restauration comprising a section of a zirconia based ceramic and a section of a lithium silicate ceramic may provide some advantages.

The zirconia based ceramic typically has a higher bending strength compared to a lithium silicate ceramic and may serve as the framework of a dental ceramic restoration. The facing or veneering of the dental ceramic restoration on the other hand can be made for the lithium silicate ceramic as lithium silicate ceramics are sometimes easier machinable compared to zirconia based ceramics.

As the present lithium silicate ceramic can be produced with a high translucency, the resulting dental restoration is highly esthetic.

Thus, the invention also relates to a dental restoration comprising at least two sections, section A and section B, section A comprising a zirconia based ceramic and section B comprising a lithium silicate ceramic as described in the present text.

EXAMPLES

Raw Materials
  Al2O3 aluminium hydroxide
  B2O3 boric acid
  Li2O lithium carbonate and lithium orthophosphate
  P2O5 lithium orthophosphate
  SiO2 quartz
  SrO strontium carbonate
  BaO barium carbonate
  Cs2O cesium carbonate
  TiO2 titan(IV)oxid
  ZrO2 zirconium oxide
  Hf2O hafnium oxide
  Sm2O3 samarium oxide
  Er2O3 erbium oxide
  Y2O3 yttrium oxide
  Dy2O3 dysprosium oxide
  VO2 vanadium(IV)oxide
  CeO2 cerium(IV)oxide
  Fe2O3 iron(III)oxide
  Na2O sodium sulfate, sodium carbonate
Analyses
Quantitative Rietveld Phase Analysis
  If desired, a quantitative Rietveld phase analysis can be done with a Bruker (Germany) AXS Type: D8Discover spectrometer. Such an analysis allows e.g. the determination of the content of crystalline phases.
Flexural Strength
  If desired, the flexural strength can be measured with a Zwick (Germany) type Z010 machine according to ISO 6872.
X-Ray Opacity
  If desired x-ray opacity can be measured with an X-ray machine (60 kV; sample thickness: 2 mm) according to ISO 6872.
Coefficient of Thermal Extension (CTE)
  If desired, CTE can be determined with a Netsch (Germany) Type DIL 402 C dilatometer according to ISO 6872 (sample size: 4.5*4.5*26 mm; heating rate: 5.00 K/min).
  If desired, the CTE value(s) can also be calculated similar to refractive indices by using additive factors as described in the literature known to the skilled person (e.g. Appen, A. A., Ber. Akad. Wiss. UDSSR 69 (1949), 841-844).

Chemical Stability

If desired, chemical stability can be tested according ISO 6872. Test specimens having a surface of 30-40 cm$^2$; (50*30 mm; 1-4 mm thickness) are typically cut and stored for 18 h in 4% acetic acid (80° C.).

Translucency/Contrast Ratio (CR)

If desired the translucency can be determined with a Macbath TD 932 System.

Samples are cut into slices (thickness: 1.50+/−0.05 mm), polished (surface roughness: 9 μm) and the translucency is measured.

Milling Properties

If desired, milling experiments can be done on a Sirona, Cerec™ Inlab machine.

Blocks from sample GK 79 (14×12×18 mm) were cut and an anterior crown was milled out of a nucleated block (650° C./20 h) and (650° C./20 H+850° C./40 min). The "blue state" block was easily to mill.

Sample Preparation

The glass melt raw materials were mixed in their stoechiometrical ratio and milled in a ball mill for about 1-4 h.

All compositions contained 0.5 wt.-% Na2SO4 as fining agent.

Coloration (e.g. shade A3 according to the Vita™ Colour Code Sytem) was achieved by adding small quantities of e.g. vanadium(IV)oxide, iron(III)oxide, erbium oxide and/or cerium(IV)oxide.

Melting Step 1: The composition containing the respective glass melt raw materials, fining agent and colouring oxides was heated in a platinum crucible at about 1500° C. for about 15 min and then crushed in water.

Melting Step 2: The frit was grinded with a porcelain pistil and re-melted for additional about 30-40 min at about 1500° C. A homogeneous molten composition was obtained.

Fining Step: The composition was heated for about 15 min at about 1560° C. in order to remove gaseous components.

The total melting time lasted for about 60 to about 70 min.

Casting Step: The material was casted in a pre-heated hexagonal boron nitride mould (pre-heating temperature about 650-750° C.).

Annealing Step: The casted material was annealed for about 1 hour at about 520° C. The material was left in the furnace and cooled down to room temperature. The size of the samples obtained was 50*30*18 mm.

The samples were heat treated in two further heating steps.

Heating Step 1 (nucleating step): for about 20 min up to about 20 h at about 640° C.

Heating Step 2 (crystallization step): for about 20 min up to about 1 h at about 840° C.

Compositions

The compositions shown in Table 1 were prepared.

TABLE 1

| | Comp. Ex. GK-70 | | GK-79 | | GK-92 | | GK-93 | | GK-107 | | GK 112 | | GK-116 | | GK-114 | |
|---|---|---|---|---|---|---|---|---|---|---|---|---|---|---|---|---|
| | mol % | wt % | mol % | wt % | mol % | wt % | mol % | wt % | mol % | wt % | mol % | wt % | mol % | wt % | mol % | wt % |
| $SiO_2$ | 71.32 | 78.81 | 67.00 | 66.44 | 66.47 | 66.35 | 66.52 | 66.51 | 69.70 | 64.85 | 66.30 | 65.67 | 66.10 | 63.17 | 66.1 | 62.08 |
| $Al_2O_3$ | 0.80 | 1.50 | 0.80 | 1.35 | 0.80 | 1.36 | 0.80 | 1.36 | 0.80 | 1.27 | 0.80 | 1.35 | 0.80 | 1.35 | 0.80 | 1.34 |
| $B_2O_3$ | — | — | — | — | — | — | — | — | 0.80 | 0.86 | — | — | — | — | — | — |
| $Li_2O$ | 23.56 | 13.00 | 25.30 | 12.49 | 26.10 | 12.98 | 26.10 | 12.99 | 17.00 | 7.88 | 25.60 | 12.63 | 26.11 | 12.94 | 25.73 | 12.66 |
| $Na_2O$ | 2.4 | 2.74 | 0.05 | 0.06 | 0.05 | 0.06 | 0.05 | 0.06 | 1.58 | 1.81 | 0.05 | 0.06 | 0.05 | 0.06 | — | — |
| $Cs_2O$ | — | — | 2.50 | 11.64 | 2.50 | 11.72 | 2.50 | 11.74 | 2.50 | 10.93 | 2.50 | 11.63 | 2.49 | 11.63 | 2.50 | 11.60 |
| SrO | — | — | — | — | 0.40 | 0.69 | 0.65 | 1.12 | 1.30 | 2.09 | 0.30 | 0.51 | 0.30 | 0.51 | 0.20 | 0.34 |
| BaO | — | — | — | — | 0.40 | 1.02 | 0.35 | 0.89 | 1.00 | 2.38 | 0.40 | 1.01 | 0.20 | 0.51 | 0.50 | 1.26 |
| $TiO_2$ | 0.30 | 0.44 | — | — | — | — | — | — | — | — | — | — | — | — | — | — |
| $ZrO_2$ | — | — | 0.60 | 1.22 | 0.55 | 1.13 | 0.30 | 0.62 | 1.20 | 2.29 | 1.00 | 2.03 | 1.08 | 2.21 | 1.30 | 2.64 |
| $HfO_2$ | — | — | — | — | — | — | — | — | — | — | — | — | — | — | — | — |
| $Y_{0.66}O$ | — | — | — | — | — | — | — | — | 1.10 | 1.28 | 0.17 | 0.37 | 0.30 | 0.59 | 0.3 | 0.37 |
| $Ce_{0.5}O$ | 0.50 | 0.79 | — | — | 1.15 | 1.65 | 1.15 | 1.65 | 1.15 | 1.53 | 1.15 | 1.64 | 1.15 | 1.64 | 1.15 | 1.63 |
| $Sm_{0.66}O$ | — | — | — | — | — | — | — | — | — | — | — | — | 0.04 | — | — | — |
| $P_2O_5$ | 1.00 | 2.61 | 1.15 | 2.70 | 1.15 | 2.72 | 1.15 | 2.72 | 1.15 | 2.53 | 1.15 | 2.69 | 1.21 | 2.85 | 1.15 | 2.69 |
| $Fe_{0.66}O$ | 0.12 | 0.12 | — | — | — | — | — | — | — | — | — | — | — | — | — | — |
| $Er_{0.66}O$ | — | — | 0.12 | 0.25 | 0.10 | 0.21 | 0.10 | 0.21 | 0.10 | 0.19 | 0.11 | 0.23 | 0.06 | 0.12 | 0.06 | 0.12 |
| $V_{0.4}O$ | — | — | 0.30 | 0.18 | 0.20 | 0.12 | 0.20 | 0.12 | 0.20 | 0.11 | 0.17 | 0.10 | 0.09 | 0.05 | 0.09 | 0.05 |
| $Dy_{0.66}O$ | — | — | — | — | — | — | — | — | — | — | — | — | — | — | — | — |
| CR | 0.71 | | 0.43 | | 0.48 | | 0.53 | | 0.58 | | 0.25 | | 0.35 | | 0.24 | |
| CTE [$10^{-6}$/K] | n.m. | | 9.79 | | n.m. | | n.m. | | n.m. | | n.m. | | n.m. | | n.m. | |

| | GK-119 | | GK-120 | | GK-121 | | GK-123 | | GK-122 | |
|---|---|---|---|---|---|---|---|---|---|---|
| | mol % | wt % | mol % | wt % | mol % | wt % | mol % | wt % | mol % | wt % |
| $SiO_2$ | 67.00 | 63.17 | 64.08 | 62.08 | 63.08 | 60.83 | 68.67 | 67.48 | 66.18 | 64.18 |
| $Al_2O_3$ | 0.80 | 1.28 | 0.80 | 1.32 | 0.80 | 1.31 | 1.00 | 1.67 | 0.80 | 1.32 |
| $B_2O_3$ | — | — | — | — | — | — | 1.00 | 1.14 | — | — |
| $Li_2O$ | 23.00 | 10.80 | 26.00 | 12.55 | 26.90 | 12.92 | 23.00 | 11.25 | 25.73 | 12.43 |
| $Na_2O$ | — | — | — | — | — | — | — | — | — | — |
| $Cs_2O$ | 2.60 | 11.51 | 2.50 | 11.37 | 2.50 | 11.32 | 2.50 | 11.54 | 2.50 | 11.34 |
| SrO | 0.98 | 0.66 | 1.50 | 2.51 | 0.40 | 0.67 | — | — | 0.20 | 0.34 |
| BaO | 1.18 | 2.83 | 1.50 | 3.71 | 2.60 | 6.41 | — | — | 0.5 | 1.24 |
| $TiO_2$ | — | — | — | — | — | — | — | — | — | — |
| $ZrO_2$ | — | — | 1.00 | 1.99 | 1.00 | 1.98 | — | — | — | — |
| $HfO_2$ | 1.20 | 3.97 | — | — | — | — | 0.33 | 1.14 | 1.30 | 4.42 |
| $Y_{0.66}O$ | — | — | — | — | — | — | — | — | 0.30 | 0.37 |
| $Ce_{0.5}O$ | 1.15 | 2.23 | — | — | 1.15 | 1.59 | — | — | 1.15 | 1.60 |
| $Sm_{0.66}O$ | — | — | — | — | — | — | — | — | — | — |

TABLE 1-continued

| | | | | | | | | | | |
|---|---|---|---|---|---|---|---|---|---|---|
| $P_2O_5$ | 1.00 | 2.23 | — | — | 1.15 | 2.62 | 1.15 | 2.67 | 1.15 | 2.64 |
| $Fe_{0.66}O$ | — | — | — | — | — | — | — | — | — | — |
| $Er_{0.66}O$ | 0.12 | 0.24 | 0.08 | 0.16 | 0.12 | 0.24 | 0.25 | 0.25 | 0.03 | 0.06 |
| $V_{0.4}O$ | 0.30 | 0.17 | 0.12 | 0.07 | 0.18 | 0.11 | 0.5 | 0 30 | 0.05 | 0.03 |
| $Dy_{0.66}O$ | — | — | — | — | — | — | 0.33 | 0.67 | — | — |
| CR | 0.14 | | 0.57 | | 0.63 | | 0.79 | | 0.27 | |
| CTE [$10^{-6}$/K] | 9.524 | | n.m. | | 11.354 | | n.m. | | 10.753 | |

| | GK-124 | | GK-125 | | GK-126 | | Comp. Ex. GK-131 | |
|---|---|---|---|---|---|---|---|---|
| | mol % | wt % | mol % | wt % | mol % | wt % | mol % | wt % |
| $SiO_2$ | 61.93 | 59.55 | 64.88 | 63.81 | 64.8 | 64.46 | 69.00 | 69.87 |
| $Al_2O_3$ | 0.80 | 1.31 | 0.80 | 1.34 | 0.5 | 0.85 | 0.3 | 1.38 |
| $B_2O_3$ | — | — | — | — | 0.5 | 0.58 | — | — |
| $Li_2O$ | 27.00 | 12.93 | 26.00 | 12.74 | 28.00 | 13.87 | 23.00 | 11.60 |
| $Na_2O$ | — | — | — | — | — | — | 0.05 | 0.06 |
| $Cs_2O$ | 2.50 | 11.29 | 2.50 | 11.55 | 2.5 | 11.68 | 0.60 | 2.85 |
| SrO | 0.40 | 0.66 | 1.80 | 3.06 | 0.2 | 0.35 | 0.975 | 1.71 |
| BaO | 2.60 | 6.34 | 0.30 | 0.75 | 0.2 | 0.51 | 1.175 | 3.04 |
| $TiO_2$ | 1.00 | 1.28 | — | — | — | — | — | — |
| $ZrO_2$ | 1.00 | 1.97 | 1.0 | 2.01 | — | — | — | — |
| $HfO_2$ | — | — | — | — | 1.00 | 3.49 | 1.20 | 4.23 |
| $Y_{0.66}O$ | — | — | — | — | — | — | 0.50 | 0.64 |
| $Ce_{0.5}O$ | 1.15 | 1.59 | — | — | 0.60 | 0.86 | 1.15 | 1.67 |
| $Sm_{0.66}O$ | — | — | — | — | — | — | — | — |
| $P_2O_5$ | 1.15 | 2.61 | 1.15 | 2.68 | 1.15 | 2.71 | 1.00 | 2.40 |
| $Fe_{0.66}O$ | — | — | — | — | — | — | 0.30 | 0.27 |
| $Er_{0.66}O$ | 0.15 | 0.30 | 0.08 | 0.16 | 0.08 | 0.17 | 0.12 | 0.25 |
| $V_{0.4}O$ | 0.20 | 0.12 | 0.12 | 0.07 | 0.15 | 0.09 | — | — |
| $Dy_{0.66}O$ | — | — | 0.10 | 0.20 | 0.20 | 0.41 | — | — |
| CR | 0.67 | | 0.40 | | 0.69 | | 0.80 | |
| CTE [$10^{-6}$/K] | n.m. | | 11.177 | | n.m. | | n.m. | |

The amount of basic oxides has been standardized to oxygen ("O"), $Y_{0.66}O$ stands for $Y_2O_3$. The same holds true for $Ce_{0.5}O$ ($CeO_2$), $Sm_{0.66}O$ ($Sm_2O_3$), $Fe_{0.66}O$ ($Fe_2O_3$), $Er_{0.66}O$ ($Er_2O_3$), $V_{0.4}O$ ($VO_2$), $Dy_{0.66}O$ ($Dy_2O_3$). This nomenclature is known to the skilled person and used in public journals like the Journal of the American Ceramic Society; n.m means "not measured".

Physical Properties

Sample GK 79:

Flexural strength: 270±29 MPa

Coefficient of Thermal Expansion: $9.79 \cdot 10^{-6}$/K

Chemical Stability: 38 μg/cm$^2$

Vickers Hardness: 609±9 HV 0.2 kg

Blocks

Two multi-layered blocks were prepared by casting the respective compositions into a mould and treating the casted composition as outlined above.

Multi-layered Block (A): using compositions GK-123// GK-120//GK-122

Multi-layered Block (B): using compositions: GK-124// GK-125//GK 122

Figure 2:
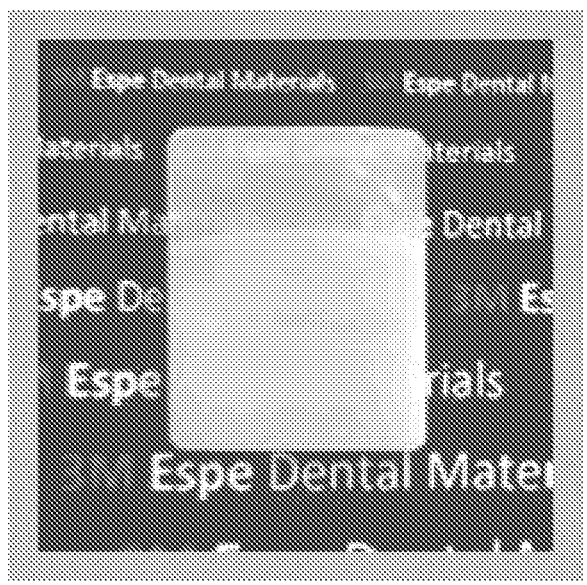
FIG. 2. is a crack free multi layered black.

During the Heating Step 1 (nucleating step) Block (A) cracked, whereas with the composition used for Block (B) it was possible to produce a crack free sample. FIGS. 1 and 2 illustrate the two combinations.

Without wishing to be bound to a certain theory, it is believed, that the difference in Delta CET is too high from the first to the second layer in Block (A) resulting in the generation of cracks.

The invention claimed is:

1. A lithium silicate glass ceramic comprising
Cs2O about 11 wt.-% and
SiO2 from about 55 to about 80 wt.-%,
Al2O3+B2O3 from about 1 to about 5 wt.-%,
Li2O from about 7 to about 16 wt.-%,
P2O5 from about 1 to about 5 wt.-%,
wt.-% with respect to the weight of the glass ceramic.

2. The lithium silicate glass ceramic according to claim 1 comprising a further metal oxide in a total amount from about 0.1 to about 10 wt.-%, the further metal oxide being selected from SrO, BaO, TiO2, ZrO2, HfO2, Fe2O3, VO2, Y2O3, CeO2, Sm2O3, Er2O3, Dy2O3, or mixtures thereof.

3. The lithium silicate glass ceramic according to claim 1 not comprising K2O, MgO, ZnO, La2O3 or a mixture of thereof in an amount above about 0.4 wt.-% with respect to the weight of the lithium silicate glass ceramic.

4. The lithium silicate glass ceramic according to claim 1 being characterized by at least one of the following parameters:
having a translucency from about 0.03 to about 0.60;
having a radiopacity of more than about 200%, determined according to ISO 6872;
having a coefficient of thermal expansion from about 8 to about $12 \times 10^{-6}$/K, determined according to ISO 6872;
having a Vickers hardness of at least about 500 (0.2 kg load);
having a flexural strength of at least about 250 MPa, determined according to ISO 6872;
having a refractive index from about 1.545 to about 1.525.

5. The lithium silicate glass ceramic according to claim 1 not comprising either of the following crystal phases in an amount above about 50% apatite, tetragonal or cubic leucite.

6. A three-dimensional article comprising a lithium silicate glass ceramic as described in claim 1, the three-dimensional article having the shape of a dental mill blank or ingot.

7. The three-dimensional article of claim 6 comprising at least two layers (I) and (II), each layer (I) and (II) comprising a lithium silicate glass ceramic, the lithium silicate glass ceramics of layer (I) having a different translucency than the lithium silicate glass ceramic of layer (II).

8. The three-dimensional article according to claim 6 comprising at least two layers (I) and (II), layer (I) comprising a lithium silicate glass ceramic (GC I) and layer (II) comprising a lithium silicate glass ceramic (GC II), the lithium silicate glass ceramics (GC I) and (GC II) having coefficients of thermal expansion (CTE I) and (CTE II) fulfilling the equation: $(CTE\ I)-(CTE\ II) \leq \pm 1.2 \times 10^{-6}/K$.

9. The three-dimensional article of claim 6 having the shape of a dental mill blank being fixed to or in a holder.

10. A method of producing a lithium silicate glass ceramic of claim 1, the method of comprising the steps of:
 a) melting a composition comprising $SiO_2$, $Li_2O$, $Al_2O_3$, $P_2O_5$, and $Cs_2O$, wherein the $Cs_2O$ is present in an amount of about 11 wt.-%,
 b) firing the composition at about 1500 to about 1600° C. for about 5 to 30 min,
 c) optionally casting the composition into a mold,
 d) annealing the composition at about 500 to about 600° C. for about 30 min to about 2 h,
 e) heating the composition to about 600 to about 700° C. for about 1 to about 30 h,
 f) heating the composition to about 750 to about 950° C. for about 5 min to about 2 h,
 g) cooling the composition down to room temperature.

11. A kit of parts comprising a part A and a part B, part A comprising a lithium silicate glass ceramic as described in claim 1 or the three-dimensional article as described in claim 6 and part B comprising a zirconia based ceramic article.

12. A dental article formed from the lithium silicate glass ceramic as described in claim 1 or the three dimensional article as described in claim 6.

13. The dental article according to claim 12 selected from crown(s), bridge(s), veneer(s), facing(s), implant(s), abutment(s), root-pin(s), orthodontic bracket(s), dental support structure(s), inlay(s), onlay(s), full arch prostheses and parts or combinations thereof.

14. A method of producing a multi-layered block, the method comprising the steps of
 melting compositions A and B of claim 11,
 casting composition A into a mold to obtain a layer I,
 cooling the composition of layer I to about 700 to about 800° C.,
 casting composition B on top of layer I to obtain a layer II,
 cooling the composition of layer II to about 700 to about 800° C.

15. A dental restoration comprising at least two sections A and B, section A comprising a zirconia based ceramic and section B comprising a lithium silicate glass ceramic as described in claim 1.

16. The lithium silicate glass ceramic according to claim 1, the three-dimensional article having the shape of a dental mill blank or ingot and comprising at least two layers (I) and (II), each layer (I) and (II) comprising a lithium silicate glass ceramic, the lithium silicate glass ceramics of layer (I) having a different translucency than the lithium silicate glass ceramic of layer (II), wherein the lithium silicate glass ceramic does not comprise either of the following crystal phases in an amount above about 50% apatite, tetragonal or cubic leucite.

17. A method of producing a lithium silicate glass ceramic, the method comprising the steps of:
 a) melting a composition of claim 1,
 b) firing the composition at about 1500 to about 1600° C. for about 5 to 30 min,
 c) optionally casting the composition into a mold,
 d) annealing the composition at about 500 to about 600° C. for about 30 min to about 2 h,
 e) heating the composition to about 600 to about 700° C. for about 1 to about 30 h,
 f) heating the composition to about 750 to about 950° C. for about 5 min to about 2 h,
 g) cooling the composition down to room temperature.

* * * * *